(12) United States Patent
Bombardelli et al.

(10) Patent No.: US 6,428,820 B2
(45) Date of Patent: Aug. 6, 2002

(54) **EXTRACTS OF *HYPERICUM PERFORATUM* AND FORMULATIONS CONTAINING THEM**

(75) Inventors: Ezio Bombardelli; Bruno Gabetta; Paolo Morazzoni, all of Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 09/725,938

(22) Filed: Nov. 30, 2000

Related U.S. Application Data

(63) Continuation of application No. PCT/EP99/03881, filed on Jun. 4, 1999.

(51) Int. Cl.⁷ .............................................. A01N 65/00
(52) U.S. Cl. ...................................................... 424/730
(58) Field of Search ......................................... 424/730

(56) References Cited

FOREIGN PATENT DOCUMENTS

| DE | 198 18 001 C1 | 8/1999 |
|---|---|---|
| EP | 0 599 307 A1 | 6/1994 |
| WO | WO 97/13489 | 4/1997 |

OTHER PUBLICATIONS

M. Brolis et al., J. of Chromatography, 825, 1998, pp. 9–16.
S. S. Chatterjee et al., Antidepressant Activity of Hypericum Perforatum and Hyperforin: The Neglected Possibility, Pharmacopsychiatry, vol. 31, Jun. 1998, pp. 7–15.
Naturally Occurring Benzodiazepines Structure, Distribution and Function; I. Izquierdo and J. Medina, Editors; 1993, pp. 33–34.
Butterweck V. et al., "Effects of the total extract and fractions of Hypericum perforatum in animal assays for antidepressant activity," Pharmacopsychiatry 30(2):117–124, 1997.
Nahrstedt A. et al., Biologically active and other chemical constituents of the herb of *Hypericum perforatum* L., Pharmacopsychiatry 30(2):129–134, 1997.

*Primary Examiner*—Herbert J. Lilling
(74) *Attorney, Agent, or Firm*—Pennie & Edmonds LLP

(57) ABSTRACT

The invention relates to a method for extracting *Hypericum perforatum* (St.-Johns-wort) by fractioning water-alcohol, alcohol extracts of the plant with esters of water-immiscible $C_1$–$C_5$ alcohols. The extracts have high activity and are stable over time. The invention also relates to formulations containing the extract.

20 Claims, No Drawings

EXTRACTS OF *HYPERICUM PERFORATUM* AND FORMULATIONS CONTAINING THEM

CROSS REFERENCE TO RELATED APPLICATIONS

The application is a continuation of the U.S. national stage of international application PCT/EP99/03881 filed Jun. 4, 1999 the content of which is expressly incorporated herein by reference thereto.

FIELD OF THE INVENTION

The present invention relates to a method for preparing an extract of *Hypericum perforatum* (St. Johns wort) by fractioning water-alcohol, alcohol, or acetone extracts of the plant with esters of water-immiscible $C_1$–$C_5$ alcohols. The invention also relates to formulations containing the extract.

BACKGROUND OF THE INVENTION

Flowering tops of *Hypericum perforatum* contain a number of classes of structurally different substances that can act directly or indirectly on the central nervous system. *Hypericum perforatum* is known to contain active compounds such as hypericin, hyperforin, and dimeric flavones that exert antidepressive and anxiolytic activities on animals and humans. The mechanisms of action of these compounds are different and include for example anti-MAO action, action on serotonin release, and activity on benzodiazepine receptors.

The activity of hypericin has been extensively discussed in the literature and includes conflicting reports on the activity of hypericin. The controversial antidepressive activity of hypericin, however, was recently confirmed in pharmacological models in vivo. It has been proven that hypericin is active when administered in the presence of dimeric procyanidins contained in the extracts of *Hypericum perforatum* (45th Annual Congress of the Society for Medicinal Plant Research, Sep. 7th–12th, 1997, Regensburg, Germany, V. Butterwecke et al., Abstract No. 011).

Hyperforin has recently been the subject of numerous studies that have established its role as antidepressant. Studies carried out by the Applicant have proven that hyperforin has serotonin-mimetic activity.

Other components of *Hypericum perforatum* that are considered important are dimeric flavones derived from apigenin which are considered to be natural benzodiazepines, as reported in "Naturally Occurring Benzodiazepines Structure, Distribution and Function", I. lzquierdo and J. Medicine Eds., 1993, page 33.

These components, and particularly hyperforin, are not stable under typical extraction conditions and storage conditions. WO 97/13489 (Schwabe) discloses that the hyperforin content of a water-alcohol extract of St.-John's-wort falls to almost zero after only a few weeks. According to WO 97/13489, in order to obtain stable extracts with a constant hyperforin content it is necessary to perform the extraction, purification and storage in the presence of antioxidants such as vitamin C and the esters thereof, sulfurated amino acids, and the like.

EP 0599307 (Schwabe) discloses the removal of hypericin, responsible for undesired photo-sensitizing effects, by means of polyvinylpyrrolidone and other chemicals.

The patent describes extracts obtained without using antioxidants and having a hyperforin content of at least 5%.

Comparative pharmacological and clinical data between conventional methanolic extracts or extracts prepared according to the monograph of Commission E with the extracts prepared according to EP 0599307 and WO 97/13489 are not available. It is recognized, however, that conventional extract of *Hypericum perforatum* contain large amounts of flavonoids, which are potent radical scavengers and therefore natural stabilizing agents for easy-to-oxidize substances, together with other substances which can significantly contribute to the activity of the extract.

SUMMARY OF THE INVENTION

The invention relates to a method of preparing stable extracts of *Hypericum perforatum*. The method includes the steps of extracting flowering tops of *Hypericum perforatum* with alcohol or acetone solvent to provide a first extract solution; filtering the first extract solution; concentrating the first extract solution to provide a concentrate; diluting the concentrate with a water or a water-alcohol solvent to provide an aqueous solution; extracting the aqueous solution with one or more aliphatic ester solvents to provide an ester extract; filtering the ester extract; and g) evaporating the solvents from the ester extract to provide a stable extract of *Hypericum perforatum*.

The method may further include the step of solubilizing the stable extract of *Hypericum perforatum* in a solvent comprising an acid in aqueous ethanol to provide an aqueous ethanol solution and evaporating the solvents from the aqueous ethanol solution at a temperature of less than 40° C. The organic acid may be citric acid, malic acid, acetylaspartic acid, phosphoric acid, or a mixture thereof. The aqueous ethanol solution may be 95 percent ethanol.

The alcohol or acetone solvent used in step (a) may be one or more of methanol or ethanol or it may be acetone. The ratio of the weight of the flowering tops to the alcohol or acetone solvent in step (a) may be from 1:2 to 1:20.

The concentrate in step (d) may be diluted with an equal volume of water or water-alcohol solvent. The concentrate may be diluted with a water-alcohol solvent having an alcohol to water volume ratio of from 1:2 to 1:5. The water-alcohol solution in step (d) may contain one or more of methanol or ethanol The volume ratio of the aqueous solution to the one or more aliphatic ester solvents in step (e) may be from 1:0.5 to 1:2. The aliphatic ester solvent in step (e) may be ethyl acetate, methyl acetate, butyl acetate, or mixtures thereof. The aliphatic ester solvent may be ethyl acetate.

The invention also relates to an extract of *Hypericum perforatum* obtained by the process of the invention. The extract may have an $IC_{50}$ for inhibition of serotonin uptake of less than 0.32 µg/ml or an $IC_{50}$ for inhibition of dopamine uptake of less than 2.72 µg/ml. The hyperforin content of the extract may be from 10 to 50 percent by weight of the extract, the total hypericin content of the extract may be greater than 0.5 percent by weight of the extract, and dimeric flavones content of the extract may be from 1 to 2 percent by weight. In another embodiment the hyperforin content is from 10 to 50 percent by weight of the extract, the total hypericin content is from 0.5 to 1.2 percent by weight of the extract, and dimeric flavones content is from 1 to 2 percent by weight.

The invention also relates to pharmaceutical compositions containing the extract of *Hypericum perforatum* prepared by the process of the invention and a pharmaceutically acceptable excipient or carrier. The pharmaceutical composition may be formulated to be a ready-to-use solution, a soft-gelatin capsule, a hard-gelatin capsule, a tablet, or a controlled-release tablet. When the pharmaceutical composition is formulated to be a ready-to-use solution, a soft-gelatin capsule, a hard-gelatin capsule, or a tablet and the extract of *Hypericum perforatum* may be present in an amount of from 10 to 100 mg. When the pharmaceutical composition is formulated to be a controlled-release tablet and the extract of *Hypericum perforatum* may be present in an amount of from 10 to 300 mg.

The invention further relates to a method of treating or preventing depression and anxiety in humans and animals by administering to a human or animal a therapeutically effective amount of the extract prepared by the process of the invention.

DETAILED DESCRIPTION OF THE PREFERRED EMBODIMENTS

It has now been found that stable, highly active extracts of *Hypericum perforatum*, containing the main compounds responsible for pharmacological activity, in particular hypericin, hyperforin, flavonoids, and xanthones, can be prepared by a process that comprises:

a) extracting the flowering tops of *Hypericum perforatum* with alcohol or acetone;

b) filtering the extracts and concentrating the extract;

c) diluting the concentrate from step (b) with water or a water/alcohol mixture;

d) extracting the aqueous mixture from step (c) with aliphatic esters;

e) filtering and evaporating the ester extracts from step (d) to dryness; and, optionally, f) solubilizing the dry residue from (e) in a solution of an organic acid in aqueous ethanol and evaporating the solvent at a temperature below 40° C.

Preferably the first extraction (step a) is carried out with methanol or ethanol; a weight/volume ratio for the flowering tops to solvent ranging from 1:2 to 1:20, preferably from 1:2 to 1:10; and a temperatures ranging from room temperature to the reflux temperature of the solvent, preferably between room temperature and 40° C.

Aliphatic esters for use in step (d) are preferably ethyl acetate, methyl acetate, and butyl acetate.

The extraction (step d) is carried out after treating the concentrated alcohol or acetone extract with an equal volume of water or with alcohol/water mixtures having alcohol:water volume ratios ranging from 1:2 to 1:5. The volume ratio of aqueous mixture to ester is not critical and can range within wide limits, but typically ranges from 1:0.5 to 1:2. The extraction is preferably carried out repeatedly, generally at least three times, using fresh aliquots of solvent.

Optional step (f) is effected by dissolving the concentrate from (e) in a solution of an organic acid such as citric, malic, acetylaspartic, or phosphoric acids in 95% ethanol.

The resulting extract of the invention, analyzed according to the procedure described in M. Brolis et al., J. of Chromatography, 825, (1998), 9–16, contains hyperforin in amounts ranging from 5 to 20% by weight when using spontaneous vegetable biomasses and in amounts from 10 to 50% by weight when using selected vegetable biomasses. In both cases, the total hypericin content is higher than 0.5% and dimeric flavones are present in amounts from 1 to 2% by weight. The content of hyperforin, hypericin, and dimeric flavones shows wide variability depending on the time at which the plant is collected, the seed content in the flowering tops, and the amount of stems present in the biomass.

This extract, compared to the total extract, surprisingly has high activity in various pharmacological models used for evaluating antidepressive and anxiolytic effects and is stable over time without further treatment. The process of the invention provides stable extracts with no need for further processing. The extracts, however, should be shielded from light to avoid photo-degradation.

Table I shows the activity of the extract of the invention compared to other extracts and compounds on the inhibition of serotonin (5-HT) and dopamine (DA) uptake.

TABLE I

Effect *Hypericum perforatum* Extract Prepared According to Example 1 at Inhibiting $^3$H 5-HT and DA Uptake.

| | $IC_{50}$ µg/ml | |
|---|---|---|
| Substance | $^3$H DA | $^3$H-5 HT |
| Alcoholic extract | 4.05 ± 0.93 | 28.0 ± 1.7 |
| Hexane extract | 0.86 ± 0.02 | 3.08 ± 0.62 |
| Example 1 | 0.32 ± 0.04 | 2.72 ± 1.1 |
| Hyperforin | 1.54 ± 0.23 | 4.75 ± 0.79 |
| Hypericin | >50 | >50 |
| Pseudo-hypericin | 1.40 ± 0.13 | 27.0 ± 1.1020 |

The data in Table I shows that the extract of the invention has a potency several times higher than hyperforin and other known extracts.

The extract of the invention showed a higher activity in in vivo tests than known products, such as alcoholic, methanolic, and hexane extracts, with or without hypericin. Moreover, the extract has proved to be more reproducible and to exhibit greater stability over time. The in vivo tests used to verify the antidepressive effect were the escape deficit development test and the inhibition of the ethanol consumption in Sardinia alcohol preferring rats, according to procedure known in literature.

In the escape deficit development test, the extract of the invention surprisingly showed a higher activity than known extracts and an activity comparable with that of known medicaments, such as imipramine. In the escape deficit development test rats are fastened and subjected to mild, short, unavoidable electric shocks for 50 min (pre-test). Twenty-four hours later, animals are tested for their ability to avoid the same stimuli on their tails, in a situation in which escape is impossible. On the average a rat makes 26 escapes out of 30 stimuli (naive controls), whereas an animal subjected to pre-test only makes 1–3 escapes (ED controls). Hyporeactivity induced by the pre-test does not take place in rats pre-treated for 1–3 weeks with antidepressants such as imipramine or fluoxetine. The St. John's-wort extracts orally administered to rats one hour before exposure to the unavoidable stress cause an increase in reactivity to the escape test, which is further enhanced when pre-treatment is effected for 1–2 weeks. Table II summarizes the antidepressive effect of *Hypericum perforatum* extracts and fractions thereof in rats in the escape test with a 2 week pre-treatment.

TABLE II

Antidepressive Effect of *Hypericum perforatum* Extracts and Fractions Thereof in Rats in the Escape Test with a 2 week Pre-treatment.

| Substance | Dose (mg/kg) | Number of escapes |
|---|---|---|
| Hypericum alcoholic extract | 1000 | 16.6 ± 2.8 |
| Hexane extract | 600 | 17.2 ± 1.6 |
| Example 1 | 200 | 23.3 ± 0.4 |
| Example 1 | 100 | 18.3 ± 0.2 |
| Example 1 | 50 | 13.3 ± 0.4 |

TABLE II-continued

Antidepressive Effect of *Hypericum perforatum* Extracts and Fractions Thereof in Rats in the Escape Test with a 2 week Pre-treatment.

| Substance | Dose (mg/kg) | Number of escapes |
|---|---|---|
| ED Controls | — | 1.6 ± 0.1 |
| Naive controls | — | 24.1 ± 0.1 |

Statistical analysis: Kruskal-Wallis non parametric ANOVA
KW = 13.462 p = 0.0012
Hypericum alcoholic extract vs naive p < 0.01
Hypericum extracted as in Example 1,200 mg/kg vs naive n.s.
Naive vs AND p < 0.01

In the test of the reduction of alcohol consumption in Sardinia rats according to procedures known in literature (which is an index of depression and anxiety), the extracts of the invention, after three days administration, induced a 75% decrease in alcohol consumption in favor of water compared with controls, whereas the reduction in alcohol consumption after treatment with methanolic or hexane extracts was 30 and 40%, respectively.

The extract of the invention can be included in formulations for oral use, such as ready-to-use solutions, soft- or hard- gelatin capsules, tablets, and controlled-release tablets. The dosage of extract in the formulations range from 10 to 100 mg per dose in the usual formulations and up to 300 mg in the controlled-release formulations, in this case the preferred dose is 300 mg per dose daily.

EXAMPLES

The examples reported hereinbelow illustrate the preferred embodiments of the present invention in greater detail but should not be construed to limit the invention in any way.

Example 1
Preparation of a Dry Extract of *Hypericum perforatum* Standardized in the Active Components 4 Kg of *Hypericum perforatum* flowering tops were extracted with 4×15 L of methanol in an extraction apparatus of 25 L capacity. The combined methanol extracts were concentrated under vacuum to 2.5 L, the concentrate diluted with an equal volume of water, and counter-extracted with 3×1.5 L of ethyl acetate. The organic phase was filtered and concentrated to dryness under vacuum and the resulting residue was dissolved in a solution of 2 g of citric acid in 1.3 L of 95% ethanol. The organic phase was then evaporated to dryness under vacuum at a temperature of less than 40° C. to provide 0.32 kg of a brown-yellow extract containing 20% of hyperforin, 0.9% of total hypericins (hypericin plus pseudohypericin), and 1% of diapigenin.

Example 2
Preparation of an Extract of *Hypericum perforatum* Standardized in the Active Components 60 kg of *Hypericum perforatum* flowering tops were collected and mechanically dried at a temperature less than 60° C. and were extracted under mild reflux with 4×20 L of acetone. The combined extracts were filtered to remove biomass residues and concentrated under vacuum to dryness to provide 3 kg of an extract containing 0.4% of total hypericins and about 25% of hyperforin. The extract was suspended in 10 L of a methanol/water mixture (3:7) and counter-extracted with butyl acetate to completely extract the polyphenols. Extraction of the polyphenols was monitored by thin layer chromatography using a silica gel support and eluting with ethyl acetate/methanol/$H_2O$ (100:13.5:10).

The aqueous phase was removed, and the organic phase dried ($Na_2SO_4$) and concentrated to dryness under vacuum at a temperature of less than 40° C. to provide 1.6 kg of dry extract containing 0.7% of total hypericins, about 40% of hyperforin, and 1.4% of dimeric flavones.

Example 3
Preparation of a Multicomponent Extract of *Hypericum perforatum*. Standardized in the Active Components.

60 kg of *Hypericum perforatum* flowering tops were collected and mechanically dried at a temperature of less than 60° C. and were continuously extracted with 98% methanol until all the extractables were removed. The methanolic extract was then concentrated to 30 L and the concentrate diluted with an equal volume of water. Insolubles that separated during dilution were removed by filtration and the resulting clear solution was extracted with 3×30 L of water-saturated ethyl acetate, dried ($Na_2SO_4$), and the solvent removed under vacuum to provide 3.8 kg of a brown extract containing 25% of hyperforin, 1.2% of total hypericin, and 1.2% of dimeric diflavones.

Example 4
Solution Containing the Lipophilic Extract of *Hypericum perforatum* Prepared According to Example 1

| | |
|---|---|
| Extract of *Hypericum perforatum* prepared according to Example 1 | 10.0 g |
| Ammonium glycyrrhizinate | 0.5 g |
| Propylene glycol | 35.0 g |
| 70% Sorbitol solution | 25.0 g |
| Purified water | q.s. to 100 ml |

Example 5
Coated Tablets Containing the Extract of *Hypericum perforatum* Prepared According to Example 2

| | |
|---|---|
| Extract of *Hypericum perforatum* prepared according to Example 2 | 300.00 mg |
| Soy polysaccharides | 54.75 mg |
| Lactose | 46.00 mg |
| Cross-linked sodium carboxymethyl cellulose | 40.00 mg |
| Silica | 20.00 mg |
| Polyvinylpyrrolidone | 5.00 mg |
| Talc | 2.50 mg |
| Magnesium stearate | 1.75 mg |
| Coating: | |
| Hydroxypropyl methylcellulose | 10.00 mg |
| Talc | 8.50 mg |
| Titanium dioxide | 5.00 mg |
| Triacetin | 2.00 mg |
| Polysorbate 80 | 0.50 mg |
| Red iron oxide | 1.00 mg |

Example 6
Soft-gelatin Capsules

| | |
|---|---|
| Extracts of *Hypericum perforatum* of Example 1 | 100 mg |
| Saccharose monopalmitate | 100 mg |
| Polyethylene glycol 400 | 220 mg |

-continued

| | |
|---|---|
| Glycerin | 15 mg |
| Purified water | 15 mg |

What is claimed is:

1. A method of preparing stable extracts of *Hypericum perforatum* comprising:
    extracting flowering tops of *Hypericum perforatum* with alcohol or acetone solvent to provide a first extract solution;
    filtering the first extract solution;
    concentrating the first extract solution to provide a concentrate;
    diluting the concentrate with a water or a water-alcohol solvent to provide an aqueous solution;
    extracting the aqueous solution with one or more aliphatic ester solvents to provide an ester extract;
    filtering the ester extract; and
    evaporating the solvents from the ester extract to provide a stable extract of *Hypericum perforatum*.

2. The method of claim 1, further comprising solubilizing the stable extract of *Hypericum perforatum* in a solvent comprising an acid in aqueous ethanol to provide an aqueous ethanol solution and evaporating the solvents from the aqueous ethanol solution.

3. The method of claim 2, wherein the organic solvents are evaporated from the aqueous ethanol solution at a temperature of less than 40° C., the organic acid is selected from the group consisting of citric acid, malic acid, acetylaspartic acid, phosphoric acid, and mixtures thereof, and the aqueous ethanol solution is 95 percent ethanol.

4. The method of claim 1, wherein the alcohol or acetone solvent is one or more of methanol or ethanol.

5. The method of claim 1, wherein the alcohol or acetone solvent is acetone.

6. The method of claim 1, wherein the flowering tops are present at a weight relative to the volume of alcohol or acetone solvent to provide a ratio of from 1:2 to 1:20.

7. The method of claim 1, wherein the concentrate is diluted with an equal volume of water or water-alcohol solvent.

8. The method of claim 1, wherein the concentrate is diluted with a water-alcohol solvent having an alcohol to water volume ratio of from 1:2 to 1:5.

9. The method of claim 1, wherein the water-alcohol solution comprises one or more of methanol or ethanol.

10. The method of claim 1, wherein the aqueous solution and one or more aliphatic ester solvents are present in a volume ratio from 1:0.5 to 1:2.

11. The method of claim 1, wherein the aliphatic ester solvent is selected from the group consisting of ethyl acetate, methyl acetate, butyl acetate, and mixtures thereof.

12. The method of claim 11, wherein the aliphatic ester solvent is ethyl acetate.

13. The stable extract of *Hypericum perforatum* obtained by the process of claim 1.

14. The extract of claim 13, wherein the extract has an $IC_{50}$ for inhibition of serotonin uptake of less than 0.32 $\mu g/ml$ or an $IC_{50}$ for inhibition of dopamine uptake of less than 2.72 $\mu g/ml$.

15. The extract of claim 13, wherein the hyperforin content is from 10 to 50 percent by weight of the extract, the total hypericin content is greater than 0.5 percent by weight of the extract, and the dimeric flavones content is from 1 to 2 percent by weight.

16. The extract of claim 13, wherein the hyperforin content is from 10 to 50 percent by weight of the extract, the total hypericin content is from 0.5 to 1.2 percent by weight of the extract, and the dimeric flavones content is from 1 to 2 percent by weight.

17. A pharmaceutical composition comprising the extract of *Hypericum perforatum* of claim 13 and a pharmaceutically acceptable excipient or carrier.

18. The pharmaceutical composition of claim 17, wherein the composition is formulated to be a ready-to-use solution, a soft-gelatin capsule, a hard-gelatin capsule, or a tablet and the extract of *Hypericum perforatum* is present in an amount of from 10 to 100 mg.

19. The pharmaceutical composition of claim 17, wherein the composition is formulated to be a controlled-release tablet and the extract of *Hypericum perforatum* is present in an amount of from 10 to 300 mg.

20. A method of treating or preventing depression and anxiety in humans and animals which comprises administering to a human or animal a therapeutically effective amount of the pharmaceutical composition of claim 17.

* * * * *